US011759411B2

(12) United States Patent
Swoboda et al.

(10) Patent No.: US 11,759,411 B2
(45) Date of Patent: Sep. 19, 2023

(54) NON-THERAPEUTIC USE OF A BIODEGRADABLE HYDROCARBON OIL

(71) Applicant: TOTAL MARKETING SERVICES, Puteaux (FR)

(72) Inventors: Benjamin Swoboda, Orgeval (FR); Philippe Lemaire, Etiolles (FR)

(73) Assignee: TOTAL MARKETING SERVICES, Puteaux (FR)

( * ) Notice: Subject to any disclaimer, the term of this patent is extended or adjusted under 35 U.S.C. 154(b) by 346 days.

(21) Appl. No.: 16/495,679

(22) PCT Filed: Mar. 16, 2018

(86) PCT No.: PCT/EP2018/056769
§ 371 (c)(1),
(2) Date: Sep. 19, 2019

(87) PCT Pub. No.: WO2018/172226
PCT Pub. Date: Sep. 27, 2018

(65) Prior Publication Data
US 2020/0093716 A1    Mar. 26, 2020

(30) Foreign Application Priority Data
Mar. 20, 2017  (EP) .................... 17305305

(51) Int. Cl.
*A61K 8/31* (2006.01)
*A61K 8/41* (2006.01)
*A61K 8/49* (2006.01)
*A61Q 5/00* (2006.01)
*A61Q 19/08* (2006.01)

(52) U.S. Cl.
CPC ............ *A61K 8/31* (2013.01); *A61K 8/416* (2013.01); *A61K 8/49* (2013.01); *A61Q 5/00* (2013.01); *A61Q 19/08* (2013.01)

(58) Field of Classification Search
CPC ........ A61K 8/31; A61K 8/062; A61K 9/0014; A61K 8/416; A61K 8/49; A61K 9/107; A61K 47/44; A61K 31/01; A61K 47/06; A61K 8/8111; A61K 9/06; A61K 9/1075; A61K 2800/10; A61K 2800/21; A61K 2800/31; A61K 2800/43; A61K 2800/48; A61K 47/10; A61K 47/186; A61K 47/22; A61K 8/042; A61K 8/8117; A61K 8/8147; A61K 8/8152; A61K 8/90; A61K 8/91; A61K 2800/522; A61K 47/12; A61K 47/14; A61K 47/18; A61K 8/064; A61K 8/361; A61K 8/92; A61K 9/2018; A61K 9/4825; A61K 2800/59; A61K 8/06; A61K 8/29; A61K 8/35; A61K 8/415; A61K 8/4946; A61K 8/4966; A61K 2300/00; A61K 2800/596; A61K 8/466; A61K 2800/30; A61K 8/442; A61K 8/737; A61K 2800/28; A61K 31/60; A61K 36/00; A61K 36/28; A61K 36/736; A61K 36/77; A61K 2800/412; A61K 8/0279; A61K 8/42; A61K 8/922; A61K 45/06; A61K 8/463; A61K 2800/262; A61K 2800/49; A61K 8/368; A61K 8/37; A61K 8/86; A61K 8/9789; A61K 8/9794; A61K 31/415; A61K 38/1767; A61K 38/47; A61K 47/02; A61K 47/26; A61K 47/42; A61K 47/46; A61K 8/365; A61K 8/44; A61K 8/89; A61K 8/891; A61K 9/0048; A61K 9/08; A61Q 19/00; A61Q 5/00; A61Q 19/08; A61Q 1/00; A61Q 13/00; A61Q 17/005; A61Q 17/04; A61Q 19/001; A61Q 1/04; A61Q 1/14; A61Q 19/10; A61Q 5/02; A61Q 5/12; A61Q 1/10; A61Q 1/02; A61Q 1/06; A61Q 19/001; A61Q 19/007; A61Q 3/00; A61Q 1/12; A61Q 3/02
See application file for complete search history.

(56) References Cited

U.S. PATENT DOCUMENTS

| | | | | |
|---|---|---|---|---|
| 2006/0039885 A1* | 2/2006 | Nishio | ........... | A61K 8/585 424/70.122 |
| 2011/0251273 A1 | 10/2011 | Oddos et al. | | |
| 2013/0039961 A1* | 2/2013 | Gonzales | ........... | A61Q 5/02 514/474 |

FOREIGN PATENT DOCUMENTS

| | | | |
|---|---|---|---|
| EP | 1 584 322 A1 | 10/2005 | |
| EP | 1 728 844 A1 | 12/2006 | |
| EP | 2 236 128 A1 | 10/2010 | |
| EP | 2 368 967 A1 | 9/2011 | |
| EP | 3 095 838 A1 | 11/2016 | |
| JP | 2015-221772 A | 12/2015 | |
| JP | 2017-503855 A | 2/2017 | |
| JP | 2017-505825 A | 2/2017 | |

(Continued)

OTHER PUBLICATIONS

International Search Report, issued in PCT/EP2018/056769, dated Jun. 7, 2018.

(Continued)

*Primary Examiner* — Audrea B Coniglio
(74) *Attorney, Agent, or Firm* — Birch, Stewart, Kolasch & Birch, LLP

(57) ABSTRACT

A method for the anti-ageing cosmetic treatment of the skin or of the hair applying a hydrocarbon oil that has a content by weight of isoparaffins ranging from 90 to 100%, a content by weight of normal paraffins ranging from 0 to 10% and a content of carbon of biological origin greater than or equal to 90% relative to the total weight of the hydrocarbon oil.

21 Claims, No Drawings

(56) References Cited

FOREIGN PATENT DOCUMENTS

| | | | | |
|---|---|---|---|---|
| JP | 2017-538744 A | 12/2017 | | |
| JP | 2018-519373 A | 7/2018 | | |
| WO | WO 2008/058664 A1 | 5/2008 | | |
| WO | WO2010/072787 A2 * | 12/2009 | ............. | A61Q 19/08 |
| WO | WO2010/072787 A2 * | 7/2010 | ............. | A61Q 19/08 |
| WO | WO 2010/072787 A2 | 7/2010 | | |
| WO | WO 2013/156493 A1 | 10/2013 | | |
| WO | WO 2014/033762 A1 | 3/2014 | | |
| WO | WO 2015/101837 A2 | 7/2015 | | |
| WO | WO 2015/126874 A1 | 8/2015 | | |
| WO | WO 2016/100742 A1 | 6/2016 | | |
| WO | WO2016/185046 A1 * | 11/2016 | ............... | C10G 3/00 |
| WO | WO 2016/185046 A1 | 11/2016 | | |
| WO | WO 2016/185047 A1 | 11/2016 | | |

OTHER PUBLICATIONS

Translation of Chinese Office Action issued in Application No. 201880023606.3 dated Apr. 1, 2022.
Nikko Chemicals Co., Ltd., New Cosmetics Handbook, Oct. 30, 2006, pp. 518-524.
Office Action issued in Japanese Patent Application No. 2019-551636, dated Aug. 30, 2022.
Office Action issued in Japanese Patent Application No. 2019-551636, dated Jan. 5, 2022.
English translation of the Chinese Office Action and Search Report for corresponding Chinese Application No. 201880023606.3, dated Feb. 17, 2023.

\* cited by examiner

NON-THERAPEUTIC USE OF A BIODEGRADABLE HYDROCARBON OIL

FIELD OF THE INVENTION

The invention relates to the non-therapeutic use of a hydrocarbon oil classed as biodegradable, of biological origin and mostly isoparaffinic as an anti-ageing agent, in particular for slowing down skin ageing and/or for preventing and/or delaying the formation of wrinkles and/or for attenuating wrinkles and/or for tightening the skin and/or for strengthening hair.

The invention also relates to a composition comprising a hydrocarbon oil classed as biodegradable, of biological origin mostly isoparaffinic and at least one quaternary ammonium.

TECHNICAL CONTEXT OF THE INVENTION

Men and women want to retain a young appearance as long as possible and therefore seek to delay or diminish the visible marks of ageing.

During the process of ageing, different signs can appear on the skin, in particular wrinkles and fine lines.

The cosmetic, dermatological or pharmaceutical markets are increasingly calling for ingredients of biological origin for the formulation of their products. Although the active ingredients, emulsifiers and biosourced vegetable oils have been highly developed in the last few years and are now widely available on the market, the biosourced active ingredients, especially hydrocarbon active ingredients of 100% biological origin, are still rare.

Until now oils with an antioxidant, anti-inflammatory effect or that make it possible to curb ageing are oxygenated oils such as triglycerides, esters, natural or synthetic alcohols. There are for example many vegetable oils, such as olive oil, Mango oil, sea buckthorn oil or cocoa oil.

However, all these oils have a substantial sensitivity to oxidation, they are not sufficiently stable, which results in changes in odour and in characteristics. The instability of these vegetable oils comes in particular from the presence, in a substantial quantity, of molecules comprising heteroatoms and/or unsaturations.

Document EP 2236128 describes a mascara composition that comprises a silicone resin powder, a volatile oil and an oily gelling agent. This document does not disclose the biosourced hydrocarbon oil defined in the present invention nor its use as an anti-ageing agent.

Document WO 2010/072787 describes a cosmetic composition comprising a retinoid compound, a polar emollient and a non-polar emollient. This document does not disclose the biosourced hydrocarbon oil defined in the present invention nor its use as an anti-ageing agent.

Therefore there remains the need to have new active ingredients, of biological origin, that make it possible to combat ageing and which have satisfactory physical-chemical and sensory characteristics in particular in terms of stability, volatility, spreading on the skin, odour, soft feel and shine, rendering it highly compatible with a use in formulation.

The applicant surprisingly found that this need can be satisfied through the use of a hydrocarbon oil of biological origin mostly comprising isoparaffins.

The present invention has for objective to provide an anti-ageing agent coming from raw material of biological origin that has satisfactory physical-chemical and sensory characteristics.

The present invention has for objective to provide a stable cosmetic composition for slowing down skin ageing and/or for preventing and/or delaying the formation of wrinkles and/or for attenuating wrinkles and/or for tightening the skin.

SUMMARY OF THE INVENTION

These objectives are achieved thanks to a new active ingredient of the hydrocarbon type.

The invention relates to the use of a hydrocarbon oil that has a content by weight of isoparaffins ranging from 90 to 100%, a content by weight of normal paraffins ranging from 0 to 10% and a content of carbon of biological origin greater than or equal to 90% relative to the total weight of the hydrocarbon oil, as an anti-ageing agent.

Preferably, the hydrocarbon oil is used for slowing down skin ageing and/or for preventing and/or delaying the formation of wrinkles and/or for attenuating wrinkles and/or for tightening the skin and/or for strengthening hair.

According to an embodiment, the use according to the invention is for a topical application.

According to an embodiment of the invention, the hydrocarbon oil comprises a content by weight of isoparaffins ranging from 90 to 100%, preferably from 95 to 100% and preferentially from 98% to 100% relative to the total weight of the hydrocarbon oil.

According to an embodiment of the invention, the hydrocarbon oil is chosen from among non-cyclic isoparaffins comprising from 14 to 18 carbon atoms.

According to an embodiment of the invention, the hydrocarbon oil comprises:
  a content by weight of normal paraffins less than or equal to 10%, preferably less than or equal to 5% and preferentially less than or equal to 2% relative to the total weight of the hydrocarbon oil; and/or
  a content by weight of naphthenic compounds less than or equal to 1%, preferably less than or equal to 0.5% and preferentially less than or equal to 100 ppm relative to the total weight of the hydrocarbon oil; and/or
  a content by weight of aromatic compounds less than or equal to 500 ppm, preferably less than or equal to 300 ppm, preferentially less than or equal to 100 ppm, more preferentially less than or equal to 50 ppm, advantageously less than or equal to 20 ppm relative to the total weight of the hydrocarbon oil.

According to an embodiment of the invention, the hydrocarbon oil has a boiling temperature ranging from 230 to 340° C., preferably from 235 to 330° C. and more preferentially from 240 to 325° C. according to the standard ASTM D86 and/or a flash point greater than or equal to 110° C. according to the standard EN ISO 2719 and/or a vapour pressure at 20° C. less than or equal to 0.01 kPa.

According to an embodiment of the invention, the hydrocarbon oil is obtained by a method of catalytic hydrogenation at a temperature from 80 to 180° C. and at a pressure from 50 to 160 bars of a deoxygenated and/or isomerised feedstock of biological origin.

According to an embodiment of the invention, the hydrocarbon oil has the form of a cosmetic or dermatological composition comprising hydrocarbon oil, preferably in a quantity ranging from 0.5 to 80%, preferentially from 1 to 50% and advantageously from 5 to 30% by weight relative to the total weight of the composition.

According to an embodiment of the invention, the cosmetic or dermatological composition comprises
- at least one fatty substance chosen from among: vegetable oils, hydrocarbon oils, vegetable butters, fatty alcohols and ethers, oily esters and alkanes and silicone oils and/or
- at least one additive.

According to an embodiment of the invention, said cosmetic or dermatological composition is an anhydrous composition, an emulsion such as a water-in-oil emulsion (W/O), an oil-in-water emulsion (O/W) or a multiple emulsion (in particular W/O/W or O/W/O), a nano-emulsion, or a dispersion or a gel.

The invention also relates to a method of anti-ageing cosmetic treatment of the skin or of the hair comprising at least one step of applying, preferably by spreading, the hydrocarbon oil as defined in the invention or the cosmetic or dermatological composition as defined in the invention.

Preferably, the method is implemented for slowing down skin ageing and/or for preventing and/or delaying the formation of wrinkles and/or for attenuating wrinkles and/or for tightening the skin and/or for strengthening hair.

The invention also has for object a composition comprising:
- at least 50% by weight, relative to the total weight of the composition, of a hydrocarbon oil comprising a content by weight of isoparaffins ranging from 90 to 100%, a content by weight of normal paraffins ranging from 0 to 10% and having a content of carbon of biological origin greater than or equal to 90% relative to the total weight of the hydrocarbon oil; and
- at least one compound of the quaternary ammonium type or of the isothiazolinone type.

According to an embodiment of the invention, the hydrocarbon oil implemented in the composition according to the invention is as defined in the invention.

According to an embodiment of the invention, the compound is of the quaternary ammonium type and said quaternary ammonium implemented in the composition according to the invention is more preferably chosen from among benzalkonium chloride and didecyldimethylammonium chloride, alone or in a mixture.

According to an embodiment of the invention, the compound implemented in the composition according to the invention represents from 0.1 ppm to 40% by weight, preferably from 0.5 ppm to 30% by weight, preferentially from 1 ppm to 20% by weight, further more preferentially from 3 ppm to 10% by weight, ideally from 5 ppm to 1% by weight of the total weight of the composition.

DETAILED DESCRIPTION OF THE INVENTION

The invention relates to the non-therapeutic use of a hydrocarbon oil as an anti-ageing agent, in terms of an active ingredient, said hydrocarbon oil comprising a content by weight of isoparaffins ranging from 90 to 100%, a content by weight of normal paraffins ranging from 0 to 10% and a content in carbon of biological origin greater than 95% relative to the total weight of the hydrocarbon oil.

The hydrocarbon oil used according to the invention makes it possible to have a cosmetic or dermatological composition that is non-irritating, biodegradable and non-odorous.

The hydrocarbon oil used according to the invention makes it possible in particular to obtain stable cosmetic or dermatological compositions, in particular thanks to the hydrocarbon oil defined in the present invention which comprises low proportions, even which is substantially or entirely free, of unsaturated compounds and/or of compounds that comprise heteroatoms.

On a preliminary basis it shall be noted that, in the description and the following claims, the expression "between" must be understood as including the limits mentioned.

Hydrocarbon Oil:

The hydrocarbon oil used according to the invention preferably comprises a content by weight of isoparaffinic compounds greater than or equal to 90%, preferentially greater than or equal to 95% and advantageously greater than or equal to 98% relative to the total weight of the hydrocarbon oil.

According to an embodiment, the isoparaffinic compounds present in the hydrocarbon oil used according to the invention comprise from 12 to 30 carbon atoms, preferably from 13 to 19 carbon atoms, more preferably from 14 to 18 carbon atoms.

The hydrocarbon oil used according to the invention preferably comprises a content by weight of normal paraffins less than or equal to 10%, preferentially less than or equal to 5% and advantageously less than or equal to 2%.

The hydrocarbon oil used according to the invention advantageously comprises a majority of isoparaffins and a minority of normal paraffins. These isoparaffins are advantageously non-cyclic isoparaffins. Preferably, the hydrocarbon oil has an isoparaffin to normal paraffin mass ratio of at least 12:1, preferentially of 15:1, and more preferentially of 20:1. Even more advantageously the hydrocarbon oil used according to the invention does not contain any normal paraffins.

According to an embodiment, the hydrocarbon oil used according to the invention preferably comprises a content by weight of isoparaffins ranging from 90 to 100% and a content in normal paraffins ranging from 0 to 10%, preferentially from 95 to 100% of isoparaffins and from 0 to 5% of normal paraffins and more preferably from 98% to 100% of isoparaffins and from 0 to 2% of normal paraffins.

According to an embodiment, the hydrocarbon oil used according to the invention preferably comprises a content by weight of isoparaffins ranging from 90 to 100% and a content in normal paraffins ranging from 0 to 10%, preferentially from 95 to 100% of isoparaffins chosen from among alkanes comprising from 14 to 18 carbon atoms, preferably comprising from 14 to 17 carbon atoms.

According to an embodiment, the hydrocarbon oil used according to the invention comprises:
- isoparaffins having 15 carbon atoms and isoparaffins having 16 carbon atoms in a combined quantity ranging from 80 to 98% by weight, relative to the total weight of the hydrocarbon oil, or
- isoparaffins having 16 carbon atoms, isoparaffins having 17 carbon atoms and isoparaffins having 18 carbon atoms in a combined quantity ranging from 80 to 98% by weight, relative to the total weight of the hydrocarbon oil, or
- isoparaffins having 17 carbon atoms and isoparaffins having 18 carbon atoms in a combined quantity ranging from 80 to 98% by weight, relative to the total weight of the hydrocarbon oil.

The hydrocarbon oil used according to the invention preferably comprises a content by weight of naphthenic compounds less than or equal to 1%, preferentially less than or equal to 0.5% and more preferentially less than or equal to 100 ppm.

According to another preferred embodiment, the hydrocarbon oil used according to the invention comprises a content by weight of isoparaffins ranging from 90 to 100%, a content by weight of normal paraffins ranging from 0 to 10% and a content by weight of naphthens less than or equal to 1%. Preferentially the hydrocarbon oil comprises a content by weight ranging from 95 to 100% of isoparaffins, from 0 to 5% of normal paraffins and a content by weight of naphthens less than or equal to 0.5%. More preferentially it comprises a content by weight ranging from 98% to 100% of isoparaffins, from 0 to 2% of normal paraffins and a content by weight of naphthens less than or equal to 100 ppm.

The hydrocarbon oil implemented according to the invention is advantageously free from aromatic compounds. For example, a content by weight of aromatic compounds is understood less than or equal to 500 ppm, preferably less than or equal to 300 ppm, preferentially less than or equal to 100 ppm, more preferentially less than or equal to 50 ppm and advantageously less than or equal to 20 ppm measured for example by UV spectrometry.

The content by weight of isoparaffins, n-paraffins, naphthens and/or aromatics of the hydrocarbon oil can be determined according to methods well known to those skilled in the art. Mention can be made by way of a non-limiting example, a method by gas chromatography.

According to another preferred embodiment, the hydrocarbon oil used according to the invention comprises a content by weight of isoparaffins ranging from 90 to 100%, a content by weight of normal paraffins ranging from 0 to 10%, a content by weight of naphthens less than or equal to 1% and a content by weight of aromatic compounds less than or equal to 500 ppm. Preferentially the hydrocarbon oil comprises a content by weight ranging from 95 to 100% of isoparaffins, from 0 to 5% of normal paraffins, a content by weight of naphthens less than or equal to 0.5% and a content by weight of aromatic compounds less than or equal to 300 ppm, preferably less than 100 ppm, preferentially less than 50 ppm, more preferentially less than 20 ppm. Also preferentially the hydrocarbon oil comprises a content by weight ranging from 95 to 100% of isoparaffins, from 0 to 5% of normal paraffins and a content by weight of aromatic compounds less than or equal to 100 ppm. More preferentially it comprises a content by weight ranging from 98% to 100% of isoparaffins, from 0 to 2% of normal paraffins, a content by weight of naphthens less than or equal to 100 ppm and a content by weight of aromatic compounds less than or equal to 100 ppm.

According to an embodiment of the invention, the hydrocarbon oil comprises a content of carbon of biological origin greater than or equal to 95%, preferably greater than or equal to 98% and preferentially of 100%.

The hydrocarbon oil implemented according to the invention also preferably has an extremely low content by weight of sulphur compounds, typically less than or equal to 5 ppm, preferentially less than or equal to 3 ppm and more preferentially less than or equal to 0.5 ppm at a level that is too low to be detected using conventional low-content sulphur analysers.

The hydrocarbon oil implemented according to the invention also has more preferably a flash point greater than or equal to 110° C., preferentially greater than or equal to 120° C. and more preferentially greater than or equal to 140° C. according to the standard EN ISO 2719. A high flash point, typically greater than 110° C. making it possible to overcome on the one hand the problems of safety during the storage and transport by avoiding a flammability that is too sensitive of the hydrocarbon oil.

The hydrocarbon oil also has more preferably a vapour pressure at 20° C. less than or equal to 0.01 kPa.

According to an embodiment, the hydrocarbon oil implemented according to the invention also preferably has a flash point greater than or equal to 110° C. according to the standard EN ISO 2719 and a vapour pressure at 20° C. less than or equal to 0.01 kPa. Preferentially the hydrocarbon oil has a flash point greater than or equal to 120° C. and a vapour pressure at 20° C. less than or equal to 0.01 kPa. And more preferentially, it has a flash point greater than or equal to 130° C. and a vapour pressure at 20° C. less than or equal to 0.01 kPa.

The hydrocarbon oil implemented according to the invention has boiling temperatures, a flash point and a vapour pressure that make it possible to overcome the problems of flammability, odour and volatility.

The hydrocarbon oil according to the invention furthermore has a kinematic viscosity at 40° C. less than or equal to 5 cSt, preferentially less than or equal to 4 cSt and more preferentially less than or equal to 3 cSt according to the standard EN ISO 3104.

Method for Obtaining:

Such compositions of hydrocarbon oils can be obtained in the following way. The hydrocarbon oil used according to the invention is a hydrocarbon fraction which comes from the conversion of biomass.

The term, coming from the conversion of biomass, means a hydrocarbon fraction produced from raw materials of biological origin.

Preferably, the hydrocarbon fraction of biological origin is obtained by a method comprising steps of hydrodeoxygenation (HDO) and of isomerisation (ISO). The step of hydrodeoxygenation (HDO) leads to the decomposition of the structures of the biological esters or of the triglyceride constituents, to the elimination of the oxygenated, phosphorus and sulphur compounds and to the hydrogenation of the olefinic bonds. The product coming from the hydrodeoxygenation reaction is then isomerised. A step of fractionation can preferably follow the steps of hydrodeoxygenation and of isomerisation. Advantageously, the fractions of interest are then subjected to steps of hydrotreatment then of distillation in order to obtain the specifications of the hydrocarbon oil desired according to the invention.

This HDO/ISO method is implemented on a raw biological feedstock, also called biomass or raw material of biological origin, selected from the group consisting of vegetable oils, animal fats, fish oils and mixtures thereof. The suitable raw materials of biological origin are for example rapeseed oil, canola oil, tallol or tall oil, sunflower oil, soybean oil, hempseed oil, olive oil, linseed oil, mustard oil, palm oil, groundnut oil, castor oil, coconut oil, animal fats such as tallow, recycled dietary fats, genetically engineered raw materials, and biological raw materials produced from microorganisms such as algae and bacteria. Condensation products, esters or other derivatives obtained from raw biological materials can also be used as raw materials.

Preferably, the raw material of biological origin is an ester or a triglyceride derivative. This material is firstly subjected to a step of hydrodeoxygenation (HDO) in order to decompose the structure of the component esters or triglycerides and eliminate the oxygenated, phosphorous and sulphur compounds concurrently to the hydrogenation of the olefinic bonds. This step of hydrodeoxygenation (HDO) of the raw material of biological origin is followed by an isomerisation of the product thus obtained leading to the branching of the hydrocarbon chain and by an improvement in the properties of the paraffin at low temperatures.

During the HDO step, the hydrogen and the raw material of biological origin are passed over a catalytic hydrodeoxygenation bed simultaneously, in the same direction or counter-current. During the HDO step, the pressure and the temperature are between 20 and 150 bars and between 200 and 500° C. respectively. Conventional and known hydrodeoxygenation catalysts are used during this step. Optionally, the raw material of biological origin can be subjected to a pre-hydrogenation under mild conditions in order to prevent the secondary reactions of double bonds before the HDO step. After the step of hydrodeoxygenation, the product coming from the reaction is subjected to a step of isomerisation (ISO) where the hydrogen and the product, and optionally a mixture of n-paraffins, are passed over catalytic hydrodeoxygenation beds simultaneously, in the same direction or counter-current. During the ISO step, the pressure and the temperature are between 20 and 150 bars and between 200 and 500° C. respectively. Conventional and known isomerisation catalysts are used during this step.

Additional secondary methods can also be implemented (such as intermediate mixtures, trappings or other methods of the sort).

The product coming from the HDO/ISO steps can optionally be fractionated in order to obtain the fractions of interest.

Various HDO/ISO methods are described in literature. Application WO2014/033762 describes a method that comprises a step of pre-hydrogenation, a step of hydrodeoxygenation (HDO) and a step of isomerisation carried out counter-current. Patent application EP1728844 describes a method of producing hydrocarbon compounds from a mixture of compounds of vegetable and animal origin. This method comprises a step of pretreating the mixture that makes it possible to remove the contaminants, such as for example alkali metal salts, followed by a step of hydrodeoxygenation (HDO) and by a step of isomerisation. Patent application EP2084245 describes a method for producing a hydrocarbon mixture that can be used as diesel or in a composition of diesel by hydrodeoxygenation of a mixture of biological origin that contains fatty acid esters optionally in a mixture with free fatty acids, for example vegetable oils such as sunflower oil, rapeseed oil, canola oil, palm oil or pine oil, followed by a hydroisomerisation on specific catalysts. Patent application EP2368967 describes such a method and the product obtained by this method. Application WO2016/185046 describes a method for obtaining a hydrocarbon oil used according to the invention, wherein the hydrocarbon oil is obtained by a method of catalytic hydrogenation at a temperature from 80 to 180° C. and at a pressure from 50 to 160 bars of a deoxygenated and isomerised feedstock of biological origin.

Advantageously, the raw material of biological origin contains less than 15 ppm by weight of sulphur, preferably less than 8 ppm, preferentially less than 5 ppm and more preferentially less than 1 ppm according to the standard EN ISO 20846. Ideally, the feedstock does not contain any sulphur as a raw material of biosourced origin.

Before the step of hydrotreatment, a step of pre-fractionating can take place. A narrower fraction at the inlet of the hydrogenation unit makes it possible to obtain a narrow fraction at the outlet of the unit. Indeed, the boiling points of pre-fractionated fractions are between 220 and 330° C. while the fractions that were not pre-fractionated typically have boiling points between 150 and 360° C.

The deoxygenated and isomerised feedstock coming from the HDO/ISO method is then hydrogenated.

The hydrogen used in the hydrogenation unit is typically highly purified hydrogen. The term highly purified means hydrogen of a purity for example greater than 99%, although other grades can also be used.

The step of hydrogenation is carried out thanks to catalysts. The typical hydrogenation catalysts can be either by mass or supported and can include the following metals: nickel, platinum, palladium, rhenium, rhodium, nickel tungstate, nickel-molybdenum, molybdenum, cobalt-molybdenum. The supports can be silica, alumina, silica-alumina or zeolites.

A preferred catalyst is a catalyst with a nickel base on an alumina support of which the specific surface area varies between 100 and 200 $m^2/g$ of catalysts or a mass catalyst based on nickel. The hydrogenation conditions are typically as follows:

Pressure: 50 to 160 bars, preferably 80 to 150 bars and more preferentially 90 to 120 bars;

Temperature: 80 to 180° C., preferably 120 to 160° C. and more preferentially 150 to 160° C.;

Liquid Hourly Space velocity (LHSV): 0.2 to 5 $hr^{-1}$, preferably 0.4 to 3 $hr^{-1}$ and more preferentially 0.5 to 0.8 $hr^{-1}$;

Treatment rate with hydrogen: adapted to the conditions mentioned hereinabove and able to range up to 200 $Nm^3$/tonne of feedstock to be treated.

The temperature in the reactors is typically between 150 and 160° C. with a pressure of about 100 bars while the hourly space velocity is about 0.6 $hr^{-1}$ with a treatment rate adapted according to the quality of the feedstock to be treated and the parameters of the first hydrogenation reactor.

The hydrogenation can take place in one or several reactors in series. The reactors can include one or several catalytic beds. The catalytic beds are generally stationary catalytic beds.

The method of hydrogenation preferably comprises two or three reactors, preferably three reactors and is more preferentially carried out in three reactors in series.

The first reactor allows for the trapping of the sulphur compounds and the hydrogenation of substantially all the unsaturated compounds and up to about 90% of the aromatic compounds. The product coming from the first reactor contains substantially no sulphur compound. At the second stage i.e. in the second reactor, the hydrogenation of the aromatics continues and up to 99% of the aromatics are therefore hydrogenated.

The third stage in the third reactor is a finishing stage that makes it possible to obtain mass contents in aromatics less than or equal to 500 ppm, preferably less than or equal to 300 ppm, preferentially less than or equal to 100 ppm, more preferentially less than or equal to 50 ppm, and ideally less than or equal to 20 ppm even in the case of products with a high boiling point for example greater than 300° C.

It is possible to use a reactor that has two or three or more catalytic beds. The catalysts can be present in variable or essentially equal quantities in each reactor; for three reactors, the quantities according to the weight can for example be of 0.05-0.5/0.10-0.70/0.25-0.85, preferably 0.07-0.25/0.15-0.35/0.4-0.78 and more preferentially from 0.10-0.20/0.20-0.32/0.48-0.70.

It is also possible to use one or two hydrogenation reactors instead of three.

It is also possible that the first reactor be comprised of twin reactors implemented alternatively. This method of operability allows in particular a facilitated loading and unloading of the catalysts: when the first reactor comprises the catalyst saturated first (substantially all the sulphur is trapped on and/or in the catalyst) it has to be changed often.

A single reactor can also be used in which two, three or more catalytic beds are installed.

It may be necessary to insert quench boxes into the recycling system or between the reactors in order to cool the effluents from one reactor to another or from one catalytic bed to another in order to control the temperatures and the hydrothermal balance of each reaction. According to a preferred embodiment, there are no cooling or quenching intermediaries.

According to an embodiment, the product coming from the method and/or the separated gases are at least partially recycled in the feeding system of the hydrogenation reactors. This dilution contributes in maintaining the exothermicity of the reaction in controlled limits, in particular in the first stage. The recycling furthermore allows for a heat exchange before the reaction and also a better control of the temperature.

The effluent of the hydrogenation unit mainly contains the hydrogenated product and hydrogen. Flash separators are used to separate the effluents into the gaseous phase, mainly residual hydrogen, and into the liquid phase, mainly the hydrogenated hydrocarbon fractions. The method can be carried out by using three flash separators, at a high pressure, one at an intermediate pressure and one at a low pressure very close to the atmospheric pressure.

The gaseous hydrogen which is collected at the top of the flash separators can be recycled in the feeding system of the hydrogenation unit or at different levels in the hydrogenation units between the reactors.

According to an embodiment, the final product is separated at atmospheric pressure. It then directly feeds a vacuum fractionation unit. Preferably, the fractionating will take place at a pressure between 10 and 50 mbars and more preferentially at about 30 mbars.

The fractionating can be carried out in such a way that it is possible to simultaneously remove various hydrocarbon fluids from the fractionating column and in that their boiling temperature can be predetermined.

By adapting the feedstock through its initial and final boiling points, the hydrogenation reactors, the separators and the fractionation unit can therefore be connected directly without it being necessary to use intermediate tanks. This integration of the hydrogenation and of the fractionating allows for an optimised thermal integration combined with a reduction in the number of devices and energy savings.

The hydrocarbon oil implemented in the invention is advantageously a hydrocarbon fraction that has a distillation range DR (in ° C.) ranging from 230° C. to 340° C., preferably from 235° C. to 330° C. and more preferentially from 240° C. to 325° C., even more preferentially from 240° C. to 290° C. or from 240° C. to 270° C. measured according to the standard ASTM D86. Preferably, the difference between the initial boiling point and the final boiling point is less than or equal to 80° C., preferentially less than or equal to 70° C., more preferentially less than or equal to 60° C. and advantageously between 40 and 50° C. The hydrocarbon oil can include one or several fractions of distillation ranges within the ranges described hereinabove.

Advantageously, the hydrocarbon oil implemented in the invention is totally saturated. Preferably, the components of the hydrocarbon oil are chosen from among isoparaffins that comprise 13 to 27 carbon atoms, preferentially 13 to 18 carbon atoms and more preferentially 14 to 18 carbon atoms.

The hydrocarbon oil used according to the invention advantageously comprises a content of isohexadecane less than or equal to 50%.

The hydrocarbon oil used according to the invention ideally comes from the treatment of raw materials of biological origin. The term "bio-carbon" indicates that the carbon is of natural origin and comes from a biomaterial, as indicated hereinafter. The content in bio-carbon and the content in biomaterial are expressions that indicate the same value. A material of renewable origin or biomaterial is an organic material wherein the carbon comes from the $CO_2$ fixed recently (on a human scale) by photosynthesis from the atmosphere. A biomaterial (Carbon of 100% natural origin) has an isotopic ratio $^{14}C/^{12}C$ greater than $10^{-12}$, typically about $1.2 \times 10^{-12}$, while a fossil material has a zero ratio. Indeed, the isotopic $^{14}C$ is formed in the atmosphere and is then integrated via photosynthesis, according to a time scale of a few tens of years at most. The half-life of the $^{14}C$ is 5,730 years. Thus, the materials coming from photosynthesis, namely plants in general, necessarily have a maximum content in isotope $^{14}C$.

The determination of the content of biomaterial or of bio-carbon is given in accordance with the standards ASTM D 6866-12, the method B (ASTM D 6866-06) and ASTM D 7026 (ASTM D 7026-04). The hydrocarbon oil used according to the invention has a content of biomaterial of at least 90%. This content is advantageously higher, in particular greater than or equal to 95%, preferably greater than or equal to 98% and advantageously equal to 100%.

In addition to a particularly high content of biomaterial, the hydrocarbon oil used according to the invention has a particularly good biodegradability. The biodegradation of an organic chemical product refers to the reduction in the complexity of the chemical compounds thanks to the metabolic activity of microorganisms. In aerobic conditions, the microorganisms transform the organic substances into carbon dioxide, water and biomass. The method OECD 306, is used for the evaluation of the biodegradability of individual substances in sea water. According to this method, the hydrocarbon oil has a biodegradability at 28 days of at least 60%, preferably of at least 70%, more preferably of at least 75%, and advantageously of at least 80%.

Use of the Hydrocarbon Oil

Hydrocarbon oil has shown to be a good anti-ageing agent. Indeed, it makes it possible to slow down ageing, in particular thanks to its antioxidant and/or anti-radical action. Hydrocarbon oil makes it possible to fight ageing and in particular ageing of the skin, and/or to prevent and/or delay the formation of wrinkles and/or to attenuate the existing wrinkles and/or to tighten the skin and/or strengthen the hair.

The present invention also describes the cosmetic use of the hydrocarbon oil as an antioxidant agent and/or anti-radical agent.

The hydrocarbon oil is more preferably applied topically, for example on the skin of the face or of the body, on the scalp or the hair. When it is applied on the hair, the hydrocarbon oil makes it possible to strengthen the hair. The hydrocarbon oil is more preferably applied on a "healthy" skin, free from wounds or inflammation.

The hydrocarbon oil can be used alone or in the form of a cosmetic or dermatological composition.

Thanks to its improved physical-chemical and sensory properties, the hydrocarbon oil used according to the invention has a very good miscibility with the other fatty substances conventionally used in the cosmetic or dermatological fields.

In particular, the hydrocarbon oil used according to the invention has good miscibility with the fatty bodies chosen from the group comprising: hydrocarbon oils of biological or petrochemical origin (other than the hydrocarbon oil used according to the invention and defined hereinabove), vegetable oils, vegetable butters, fatty alcohols and ethers, oily esters, alkanes and silicone oils.

Hydrocarbon oils are fatty substances coming from petrochemical methods. By way of example, mention can be made of mineral oils, isoparaffins, waxes, paraffins, polyisobutenes or polydecenes.

Examples of vegetable oils are in particular wheat germ, sunflower, grape seed, sesame, corn, apricot, castor, shea, avocado, olive, soybean oil, sweet almond, palm, rapeseed, cotton, hazelnut, macadamia, jojoba, alfalfa, poppy, squash, sesame, pumpkin, rapeseed, blackcurrant, evening primrose, millet, barley, *quinoa*, rye, safflower seed, candlenut, passion flower, rose hip or *camellia* oils.

Vegetable butters are fatty substances that have the same properties as vegetable oils. The difference between the two consists in the fact that butters are in solid form at ambient temperature. Also, contrary to vegetable oils, the raw material from which a butter is extracted (pulp, seeds or almonds) is heated after having been ground for the extraction of the fat. As vegetable oils, butters can be refined in order to provide better preservation, neutralise odours, improve the colour and the consistency. Rich in antioxidants and nourishing, vegetable butters have cosmetic properties that improve the elasticity of the skin, protect from external aggressions by leaving a protective film on the epidermis and thus reducing dehydration, repair and soothe by regenerating the natural hydrolipidic film of the skin. Examples of vegetable butters are in particular shea butter, cocoa butter, mango butter, shorea butter or olive butter.

Fatty alcohols and ethers are fatty waxy long-chain substances with remarkable properties in particular film-forming, emollient, moisturising, softening and protective properties. They act as moisturising oils and as emulsifiers. Examples of fatty alcohols or ethers are: cetyl Alcohol, Stearyl Alcohol, myristyl alcohol, lauryl alcohol, behenyl alcohol, cetearyl alcohol, dicaprylyl ethers, stearyl ethers or octyldodecanol (identified by their INCI name).

Oily esters or esterified oils are the product of a reaction between fatty acids (longer chain acids, such as for example stearic acid, oleic acid, palmitic acid) and alcohols (fatty alcohols or polyols such as glycerol). These oils can contain substances coming from petrochemicals, such is the case for Isopropyl Palmitate. Examples of oily esters are caprylic capric triglyceride, coco caprylate caprate, oleyl erucate, oleyl linoleate, decyl oleate or PPG-3 benzyl ether myristate (identified by their INCI name).

The term silicone oils or polysiloxanes means an oil comprising at least one silicon atom, and in particular at least one Si—O group. As silicone oil, mention can be made in particular of phenylpropyldimethylsiloxysilicate, dimethicones or cyclopentasiloxane (identified by their INCI name).

The hydrocarbon oil used according to the invention can also be mixed with any adjuvant or additive that is normally used in the cosmetic or dermatological fields. Of course, those skilled in the art will make sure to choose the optional additive or additives of the composition in a way such that the advantageous properties attached are not or are not substantially, altered by the considered addition. Among the conventional additives able to be contained (according to the water-soluble or liposoluble nature of these adjuvants), mention can be made in particular of anionic foaming surfactants (such as sodium lauryl ether sulphate, sodium alkyl phosphate, sodium trideceth sulphate), amphoteric surfactants (such as alkyl betaine, disodium cocoamphodiacetate) or non-ionic surfactants with an HLB greater than 10 (such as POE/PPG/POE, Alkylpolyglucoside, polyglyceryl-3hydroxylauryl ether); preservatives of the quaternary ammonium type such as benzalkonium chloride or of the aromatic alcohol type such as phenoxyethanol or of the isothiazolinone type such as methylisothiazolinone; sequestering agents (EDTA); antioxidants; perfumes; dyestuffs such as soluble dyes, pigments and nacres; mattifying, tensor, whitening or exfoliating fillers; sunscreen filters; cosmetic or dermatological active ingredients and agents that have for effect to improve the cosmetic properties of the skin, hydrophilic or lipophilic (other than the hydrocarbon oil defined in the present invention); electrolytes; hydrophilic or lipophilic, anionic, non-ionic, cationic or amphoteric, thickener, gelling or dispersing polymers. The quantities of these various adjuvants are those conventionally used in the field considered, and for example from 0.01 to 20% of the total weight of the composition. As active ingredients that can be used with the hydrocarbon oil used in the invention, mention can be made of for example, water-soluble or liposoluble vitamins such as vitamin A (retinol or beta-carotene), vitamin E (tocopherol), vitamin C (ascorbic acid), vitamin B5 (panthenol), vitamin B3 (niacinamide), the derivatives of these vitamins (in particular esters) and mixtures thereof; glutathione; antiseptics; antibacterial active ingredients such as 2,4,4'-trichloro-2'-hydroxy diphenyl ether (or triclosan), 3,4,4'-trichlorocarbanilide (outriclocarban); anti-seborrheics; antimicrobials such as benzoyl peroxide, niacin (vit. PP); slimming agents such as caffeine; optical brighteners, and any active ingredient for the final purpose of the composition, and mixtures thereof.

The cosmetic or dermatological composition can thus include the hydrocarbon oil described hereinabove as a cosmetic active ingredient, at least one fatty substance chosen from among: vegetable oils, vegetable butters, fatty alcohols and ethers, oily esters, alkanes and silicone oils and at least one additive chosen from among the aforementioned additives.

This cosmetic or dermatological composition comprises a physiologically acceptable medium, i.e. which does not have any deleterious secondary effects and in particular which does not produce any unacceptable redness, flare-ups, tightness or stinging for a user. This medium optionally comprises water and/or at least one oil as a fatty substance, in addition to the aforementioned hydrocarbon oil.

According to an embodiment the cosmetic or dermatological composition has a content of hydrocarbon oil as described hereinabove ranging from 0.5 to 80%, preferably from 1 to 50% and advantageously from 5 to 30% by weight relative to the total weight of the composition.

The cosmetic or dermatological composition used according to the invention can thus be an anhydrous composition, an emulsion such as a water-in-oil emulsion (W/O), an oil-in-water emulsion (O/W) or a multiple emulsion (in particular W/O/W or O/W/O), a nano-emulsion, or a dispersion or a gel.

The cosmetic or dermatological composition used according to the invention can have the form of a more or less flexible creme or of a vaporizable emulsion.

The hydrocarbon oil or the composition that comprises it used according to the invention is advantageously characterised by the fact that it has a stability of a duration greater than or equal to 4 weeks, advantageously greater than or equal to 6 weeks, with the stability being evaluated after storage without stirring at ambient temperature, at 40° C. and at 50° C. and corresponding to a visual evaluation of the coloration and of the aspect as well as an olfactory evaluation and/or a measurement of the viscosity.

Method of Cosmetic Treatment:

The invention also relates to a method of anti-ageing cosmetic treatment of the skin or of the hair comprising at least one step of applying, preferably by spreading, the hydrocarbon oil defined in the present invention or the cosmetic or dermatological composition defined in the present invention.

The method of cosmetic treatment according to the invention makes it possible to slow down the ageing of the skin and/or prevent and/or delay the formation of wrinkles and/or to attenuate wrinkles and/or to tighten the skin and/or to strengthen hair.

Composition:

Finally, the invention relates to a composition comprising:
- at least 50% by weight, relative to the total weight of the composition, of a hydrocarbon oil comprising a content by weight of isoparaffins ranging from 90 to 100%, a content by weight of normal paraffins ranging from 0 to 10% and having a content of carbon of biological origin greater than or equal to 90% relative to the total weight of the hydrocarbon oil; and
- at least one compound of the quaternary ammonium type or of the isothiazolinone type.

According to an embodiment, the hydrocarbon oil implemented in the composition according to the invention has one or several of the characteristics defined hereinabove for the hydrocarbon oil used according to the invention.

The compounds of the quaternary ammonium type or of the isothiazolinone type are generally used as a preservative in the cosmetic, dermatological or pharmaceutical compositions. Preferably, the compound is of the quaternary ammonium type and the quaternary ammonium of the composition according to the invention can for example be chosen from among benzalkonium chloride (BAC), didecyldimethylammonium chloride, etc. Preferably, the compound of the quaternary ammonium type is benzalkonium chloride.

Among the compounds of the isothiazolinone type, mention can be made of methylisothiazolinone.

According to an embodiment of the invention, the compound, in particular the quaternary ammonium, implemented in the composition according to the invention represents from 0.1 ppm to 40% by weight, preferably from 0.5 ppm to 30% by weight, preferentially from 1 ppm to 20% by weight, further more preferentially from 3 ppm to 10% by weight, ideally from 5 ppm to 1% by weight of the total weight of the composition.

According to an embodiment, the hydrocarbon oil implemented in the composition according to the invention represents at least 60% by weight, preferably at least 70% by weight, preferentially at least 80% by weight, even more preferentially at least 90% by weight, ideally at least 99% by weight, of the total weight of the composition.

According to an embodiment of the invention, the composition comprises a major quantity of hydrocarbon oil defined in the present invention and a minor quantity of compounds of the quaternary ammonium or isothiazolinone type, in particular of the quaternary ammonium type.

The term "major quantity" means a quantity of at least 50% by weight, relative to the total weight of the composition.

The term "minor quantity" means a quantity strictly less than 50% by weight, relative to the total weight of the composition.

According to an embodiment of the invention, the composition comprises at least 60% by weight, preferably at least 70% by weight, preferentially at least 80% by weight, even more preferentially at least 90% by weight, ideally at least 99% by weight of hydrocarbon oil and less than 40% by weight, preferably less than 30% by weight, preferentially less than 20% by weight, even more preferentially less than 10% by weight, ideally less than 1% by weight of compounds of the quaternary ammonium type or of the isothiazolinone type, with said compounds being more preferably chosen from among benzalkonium chloride and methylisothiazolinone, with the percentages being expressed relative to the total weight of the composition.

According to an embodiment of the invention, the composition comprises at least 60% by weight, preferably at least 70% by weight, preferentially at least 80% by weight, even more preferentially at least 90% by weight, ideally at least 99% by weight of hydrocarbon oil and less than 40% by weight, preferably less than 30% by weight, preferentially less than 20% by weight, even more preferentially less than 10% by weight, ideally less than 1% by weight of quaternary ammonium, said quaternary ammonium being more preferably benzalkonium chloride (BAC), with the percentages being expressed relative to the total weight of the composition.

The inventors have surprisingly observed that the composition according to the invention, in particular the combination of the hydrocarbon oil classed as biodegradable, of biological origin and mostly isoparaffinic and of a preservative of the quaternary ammonium type or of the aromatic alcohol type or of the isothiazolinone type made it possible to block the production of free radicals and therefore to have an anti-age effect, in particular an anti-ageing and/or anti-wrinkle effect.

EXAMPLES

In the rest of the present description, examples are given for the purposes of information of the present invention and do not aim in any case to limit the scope thereof.

Hydrocarbon Oils Tested:

Table 1 groups together the physical-chemical properties of the various hydrocarbon oils evaluated. The oils A and B are hydrocarbon oils used according to the invention.

TABLE 1

| Characteristics | Oil A | Oil B |
| --- | --- | --- |
| Aromatics (ppm) | <20 | <20 |
| Sulphur (ppm) | 0.1 | 0.11 |
| % iso paraffins (w/w) | 98.9 | 96.2 |
| % n-paraffins (w/w) | 1.1 | 3.8 |
| % naphthenics (w/w) | 0 | 0 |
| C13 (iso) | 0.66 | 0 |
| C14 (iso) | 4.15 | 0 |
| C15 (iso) | 48.35 | 0 |
| C16 (iso) | 42.80 | 1.58 |
| C17 (iso) | 2.52 | 14.17 |
| C18 (iso) | 0.38 | 79.69 |
| C19 (iso) | 0 | 0.12 |
| C20 (iso) | 0 | 0.38 |
| C27 (iso) | 0 | 0.29 |
| Quantity of carbons of biological origin (%) | >98 | >98 |
| Initial boiling point (° C.) | 247.0 | 293.6 |
| Boiling point 5% (° C.) | 255.7 | 296.7 |
| Boiling point 50% (° C.) | 258.9 | 298.5 |

TABLE 1-continued

| Characteristics | Oil A | Oil B |
|---|---|---|
| Boiling point 95% (° C.) | 266.8 | 305.3 |
| Final boiling point (° C.) | 269.0 | 324.1 |
| OECD biodegradability (28 days) (%) | 80 | 83 |
| Refractive index at 20° C. | 1.4336 | 1.4394 |
| Density at 15° C. (kg/m³) | 776.4 | 787.2 |
| Flash point (° C.) | 115 | 149 |
| Kinematic Viscosity at 40° C. (cSt) | 2.49 | 3.87 |
| Vapour pressure at 20° C. (kPa) | <0.01 | <0.01 |
| Aniline point (° C.) | 93.2 | 99.5 |

The following standards and methods were used to measure the properties hereinabove:
flash point: EN ISO 2719
density at 15° C.: EN ISO 1185
viscosity at 40° C.: EN ISO 3104
aniline point: EN ISO 2977
boiling point: ASTM D86
biodegradability: OECD method 306
refractive index at 20° C.: ASTM D 1218
vapour pressure: calculated according to methods well known to those skilled in the art Tests for Anti-Wrinkle or Anti-Ageing Cosmetic Applications Preparation of the Tests:
Preparation of the microplates: 24 hours before the incubation with the oils A and B, the HaCaT cells are inoculated with a cell density of 100,000 cells/ml in 96-well microplates (Corning). The microplates are then placed in the incubator at 37° C. In a microplate, each condition was tested at least three times. Each experiment was carried out at least three times independently in order to validate the reproducibility of the results and to carry out statistical analyses.
Incubation of cells with the oils A or B: two durations of incubation were selected for the products to be tested pure: an incubation for fifteen minutes and an incubation for one hour. After these incubation times, the microplates are emptied, the cells are rinsed and incubated for 24 hours with the culture medium DMEM (Dulbecco's modified Eagle's medium) enriched with 10% of FBS (Foetal Bovine Serum) containing 1% by weight of glutamine and 0.5% by weight of antibiotics.

Analysis

The cellular effects are evaluated directly on the adherent living cells by cytofluorimetric microtitration (MiFALC tests-Microtitration Fluorimetric Assays on Live Cells). The microplate reader used in the study is the Safire cytometer (Tecan).

1. Evaluation of the Oxidative Stress

The oxidative stress corresponds to an imbalance between oxidising species (mainly reactive oxygen species) and antioxidant defence mechanisms. This imbalance leads to deleterious effects of the inflammation, cell degeneration, etc. type The test H2DCF-DA (2',7'-dihydrodichlorofluoresceine diacetate) is used in order to evaluate the production of reactive oxygen species. This fluorogenic molecule enters into the cells via passive diffusion and accumulates in the cytosol where it will be hydrolysed by the cellular esterases. In the presence of reactive oxygen species, the product formed can be oxidised into a fluorescent derivative. Thus, an increase in the intensity of fluorescence is combined with an increase in the production of reactive oxygen species (ROS) and by extrapolation with an increase in the oxidative stress in the cells studied.

1.1. Example 1

The production of reactive oxygen species (ROS) expressed as a percentage relative to the culture medium (CM) is indicated in table 2 hereinbelow.

TABLE 2

| Production of reactive oxygen species (% relative to the CM) | | CM | Oil A | Oil B |
|---|---|---|---|---|
| Production of ROS | Incubation 15 min H2DCF-DA | 100 | 84* | 88 |
| | Incubation 1 h H2DCF-DA | 100 | 73* | 100 |

*$p < 0.05$;
**$p < 0.01$.

As shown in table 2, the hydrocarbon oils defined in the present invention do not induce any overproduction of reactive oxygen species whatsoever after 15 minutes or after 1 hour. The oils A and B reduce the production of reactive oxygen species relative to the control culture medium.

Thus, the hydrocarbon oil defined in the present invention can be used as an anti-wrinkle or anti-ageing agent.

1.2. Example 2

Preservatives, used as an additive in cosmetic compositions, were evaluated. The preservatives evaluated are phenoxyethanol (POE) and methylisothiazolinone (MIT).

For this test, the HaCat cells are incubated with the oils A or B (for example for 15 minutes for the test with POE) then with the preservative POE or MIT (for example for 30 minutes with a solution of phenoxyethanol at 250 µg/mL).

The production of ROS is indicated in table 2bis hereinbelow.

TABLE 2bis

| Production of reactive oxygen species (% relative to the CM) | | | | | | |
|---|---|---|---|---|---|---|
| | CM | CM + POE | Oil A + POE | Oil B + POE | MIT | Oil A + MIT | Oil B + MIT |
| Production of ROS | 100 | 132 | 79 | 85 | 135 | 67 | 88 |

As shown in table 2bis, the oils A and B used according to the present invention decrease the production of reactive oxygen species in the presence of a preservative, which tends to increase the production of ROS.

2. Evaluation of the Cellular Anti-Degeneration 2.1. Evaluation of the Condensation of the Chromatin For this test, the HaCat cells are incubated for one hour with the oils A or B or with the olive oil then for 20 minutes with the benzalkonium chloride (BAC), present in a content of 8 ppm by weight. The HOECHST 33342 test is carried out in order to evaluate the condensation of the chromatin.

The benzalkonium chloride generates a phenomenon of apoptosis (programmed cell death). Olive oil (OO) is an oil known for the cellular protection against benzalkonium chloride.

The measurement of the condensation of the chromatin expressed as a percentage relative to the culture medium (CM) is indicated in table 3 hereinbelow.

TABLE 3

Measurement of the condensation of the chromatin (% relative to the CM)

| | CM | CM + BAC | OO | OO + BAC | Oil A | Oil A + BAC | Oil B | Oil B + BAC |
|---|---|---|---|---|---|---|---|---|
| Measurement | 100 | 138*** | 96 | 112 | 91 | 100 | 86 | 94 |

***p < 0.001

As shown in table 3, the oil A and B has an anti-apoptotic effect. Furthermore, it can be noted that the apoptotic effect of the benzalkonium chloride is greatly reduced in the presence of the hydrocarbon oil A or B, with this reduction being much greater than that obtained with olive oil.

2.2. Evaluation of the Activation of the Receptor P2X7

The P2X7 receptors, present in many tissues, including the skin, are involved in the phenomena of inflammation and of cell death, in particular by apoptosis.

The test YO-PRO-1 makes it possible to evaluate the activation of the P2X7 receptors. This fluorescent sensor enters into the cells only if the membrane permeability has been modified via the activation of the P2X7 receptors (opening of membrane pores). The sensor used can then be fixed onto the DNA and emit a fluorescence. The more substantial the activation of the P2X7 is, the higher the intensity of the fluorescence is.

The activation of the P2X7 expressed as a percentage relative to the culture medium (CM) is indicated in table 4.

TABLE 4

Activation of the P2X7 (% relative to the CM)

| | | CM | Oil B |
|---|---|---|---|
| Activation of the P2X7 | Incubation 15 min YO-PR0-1 | 100 | 109 |
| | Incubation 1 h YO-PR0-1 | 100 | 135* |

*p < 0.05

As shown in table 4, the hydrocarbon oil B according to the invention makes it possible to reduce the activation of the P2X7 receptor.

Thus, the hydrocarbon oil defined in the present invention has an anti-apoptotic effect, which blocks the phenomenon of cell death.

Thus, the hydrocarbon oil defined in the present invention can for example be used as an anti-wrinkle or anti-ageing agent.

The invention claimed is:

1. A method for the anti-ageing cosmetic treatment of the skin or of the hair comprising at least one step of applying a composition comprising:
   at least 90% by weight, relative to the total weight of the composition, of a hydrocarbon oil that has a content by weight of isoparaffins ranging from 90 to 100%, a content by weight of normal paraffins ranging from 0 to 10% and a content of carbon of biological origin greater than or equal to 90% relative to the total weight of the hydrocarbon oil, wherein the hydrocarbon oil has a biodegradability at 28 days of at least 60% according to OECD 306 method; and
   at least one compound of the quaternary ammonium type or of the isothiazolinone type, in an amount of less than 10% by weight.

2. The method according to claim 1, for slowing down skin ageing and/or for preventing and/or delaying the formation of wrinkles and/or for attenuating wrinkles and/or for tightening the skin and/or for strengthening hair.

3. The method according to claim 1, for a topical application.

4. The method according to claim 1, wherein the hydrocarbon oil comprises a content by weight of isoparaffins ranging from 95 to 100% relative to the total weight of the hydrocarbon oil.

5. The method according to claim 1, wherein the hydrocarbon oil is chosen from among non-cyclic isoparaffins comprising from 14 to 18 carbon atoms.

6. The method according to claim 1, wherein:
   the hydrocarbon oil comprises a content by weight of normal paraffins less than or equal to 5% relative to the total weight of the hydrocarbon oil; and/or
   the hydrocarbon oil comprises a content by weight of naphthenic compounds less than or equal to 1%, relative to the total weight of the hydrocarbon oil; and/or
   the hydrocarbon oil comprises a content by weight of aromatic compounds less than or equal to 500 ppm, relative to the total weight of the hydrocarbon oil.

7. The method according to claim 1, wherein the hydrocarbon oil has a boiling temperature ranging from 230 to 340° C., according to the standard ASTM D86 and/or a flash point greater than or equal to 110° C. according to the standard EN ISO 2719 and/or a vapour pressure at 20° C. less than or equal to 0.01 kPa.

8. The method according to claim 1, wherein the hydrocarbon oil is obtained by a method of catalytic hydrogenation at a temperature from 80 to 180° C. and at a pressure from 50 to 160 bars of a deoxygenated and/or isomerised feedstock of biological origin.

9. The method according to claim 1, wherein the step of applying is a step of spreading.

10. The method for treatment according to claim 1, for slowing down skin ageing and/or for preventing and/or delaying the formation of wrinkles and/or for attenuating wrinkles and/or for tightening the skin and/or for strengthening hair.

11. A composition comprising:
   at least 90% by weight, relative to the total weight of the composition, of a hydrocarbon oil comprising a content by weight of isoparaffins ranging from 90 to 100%, a content by weight of normal paraffins ranging from 0 to 10% and having a content of carbon of biological origin greater than or equal to 90% relative to the total weight of the hydrocarbon oil, wherein the hydrocarbon oil has a biodegradability at 28 days of at least 60% according to OECD 306 method; and
   at least one compound of the quaternary ammonium type or of the isothiazolinone type, in an amount of less than 10% by weight.

12. The composition according to claim 11, wherein at least one of the following is true:
   the hydrocarbon oil comprises a content by weight of isoparaffins ranging from 95 to 100% relative to the total weight of the hydrocarbon oil;
   the hydrocarbon oil is chosen from among non-cyclic isoparaffins comprising from 14 to 18 carbon atoms;

the hydrocarbon oil comprises a content by weight of normal paraffins less than or equal to 5% relative to the total weight of the hydrocarbon oil;

the hydrocarbon oil comprises a content by weight of naphthenic compounds less than or equal to 1%, relative to the total weight of the hydrocarbon oil;

the hydrocarbon oil comprises a content by weight of aromatic compounds less than or equal to 500 ppm, relative to the total weight of the hydrocarbon oil;

the hydrocarbon oil has a boiling temperature ranging from 230 to 340° C., according to the standard ASTM D86 and/or a flash point greater than or equal to 110° C. according to the standard EN ISO 2719 and/or a vapour pressure at 20° C. less than or equal to 0.01 kPa;

the hydrocarbon oil is obtained by a method of catalytic hydrogenation at a temperature from 80 to 180° C. and at a pressure from 50 to 160 bars of a deoxygenated and/or isomerised feedstock of biological origin.

13. The composition according to claim 11, wherein the compound is of the quaternary ammonium type.

14. The composition according to claim 13, wherein the quaternary ammonium is chosen from among benzalkonium chloride and didecyldimethylammonium chloride, alone or in a mixture.

15. The composition according to claim 11, wherein the compound represents from 0.1 ppm to 1% by weight of the total weight of the composition.

16. Method according to claim 1, wherein it involves an anti-ageing effect on the skin or hair.

17. A composition, comprising:
at least 90% by weight, relative to the total weight of the composition, of a hydrocarbon oil comprising a content by weight of isoparaffins ranging from 90 to 100%, a content by weight of normal paraffins ranging from 0 to 10% and having a content of carbon of biological origin greater than or equal to 90% relative to the total weight of the hydrocarbon oil, wherein the hydrocarbon oil has a biodegradability at 28 days of at least 60% according to OECD 306 method; and
at least one compound of the isothiazolinone type, in an amount of less than 10% by weight.

18. The composition according to claim 17, wherein at least one of the following is true:
the hydrocarbon oil comprises a content by weight of isoparaffins ranging from 95 to 100% relative to the total weight of the hydrocarbon oil;
the hydrocarbon oil is chosen from among non-cyclic isoparaffins comprising from 14 to 18 carbon atoms;
the hydrocarbon oil comprises a content by weight of normal paraffins less than or equal to 5% relative to the total weight of the hydrocarbon oil;
the hydrocarbon oil comprises a content by weight of naphthenic compounds less than or equal to 1%, relative to the total weight of the hydrocarbon oil;
the hydrocarbon oil comprises a content by weight of aromatic compounds less than or equal to 500 ppm, relative to the total weight of the hydrocarbon oil;
the hydrocarbon oil has a boiling temperature ranging from 230 to 340° C., according to the standard ASTM D86 and/or a flash point greater than or equal to 110° C. according to the standard EN ISO 2719 and/or a vapour pressure at 20° C. less than or equal to 0.01 kPa;
the hydrocarbon oil is obtained by a method of catalytic hydrogenation at a temperature from 80 to 180° C. and at a pressure from 50 to 160 bars of a deoxygenated and/or isomerised feedstock of biological origin.

19. The composition according to claim 17, wherein the compound represents from 0.1 ppm to 1% by weight of the total weight of the composition.

20. A composition comprising:
at least 90% by weight, relative to the total weight of the composition, of a hydrocarbon oil comprising a content by weight of isoparaffins ranging from 90 to 100%, a content by weight of normal paraffins ranging from 0 to 10% and having a content of carbon of biological origin greater than or equal to 90% relative to the total weight of the hydrocarbon oil, wherein the hydrocarbon oil has a biodegradability at 28 days of at least 60% according to OECD 306 method; and
at least one compound of the quaternary ammonium type or of the isothiazolinone type, in an amount of less than 10% by weight,
wherein the hydrocarbon oil has a kinematic viscosity at 40° C. less than or equal to 5 cSt.

21. The composition according to claim 11, wherein the hydrocarbon oil comprises a content of isohexadecane less than or equal to 50% by weight.

* * * * *